United States Patent [19]

Schulte et al.

[11] Patent Number: 5,059,693

[45] Date of Patent: Oct. 22, 1991

[54] PROCESS FOR MAKING 3-AROYL-2-OXINDOLE-1-CARBOXAMIDES

[75] Inventors: Gary R. Schulte, Stonington; Frederick J. Ehrgott, Norwich, both of Conn.

[73] Assignee: Pfizer Inc., New York, N.Y.

[21] Appl. No.: 417,988

[22] Filed: Oct. 6, 1989

[51] Int. Cl.$^5$ .................. C07D 405/06; C07D 409/06
[52] U.S. Cl. .................................................. 548/468
[58] Field of Search ........................................ 548/468

[56] References Cited

U.S. PATENT DOCUMENTS 4,039,591  8/1977  Close et al. ........................ 568/875
4,556,672  12/1985  Kadin ................................. 548/468
4,824,956  4/1989  Dockner et al. ...................... 549/70

OTHER PUBLICATIONS

E. Moilanen et al., Chem. Abstracts, vol. 110, No. 185555r (1989).

A. Lehninger, Biochemistry, p. 281, Worth Publishers, Inc., N.Y. (1970).

Primary Examiner—Mary E. Ceperley
Attorney, Agent, or Firm—Peter C. Richardson; J. Trevor Lumb; James M. McManus

[57] ABSTRACT

Process for making antiinflammatory 3-aroyl-2-oxindole-1-carboxamides by reductive debromination or deiodination of 3-(bromo- or iodoaroyl)-2-oxindole-1-carboxamides.

7 Claims, No Drawings

PROCESS FOR MAKING 3-AROYL-2-OXINDOLE-1-CARBOXAMIDES

BACKGROUND OF THE INVENTION

This invention relates to a new process for making certain antiinflammatory 3-[hydroxy-2-(aryl)methylene]-2-oxo-1H-indole-1-carboxamides. More particularly, it relates to production of said compounds by reductive debromination or deiodination of 3-(bromo- and/or iodo-substituted)aroyl-2-oxindole-1-carboxamides.

Prior to this invention, 3-[hydroxy-2-(aryl)methylene]-2-oxo-1H-indole-1-carboxamides have been prepared according to one of the routes indicated below in sequence A:

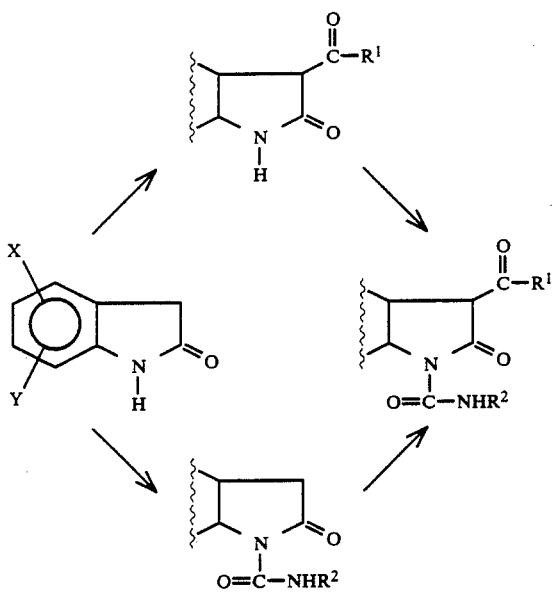

In the above reaction sequences, each of variables X, Y, $R^1$ and $R^2$ represents a wide range of substituents. Representative values of X are hydrogen, alkyl, cycloalkyl, alkoxy, alkylthio, trifluoromethyl, alkylsulfinyl, alkylsulfonyl, alkanoyl, benzoyl, thenyl, halo and alkanamido; of Y are hydrogen, halo, alkyl, alkoxy, cycloalkyl and trifluoromethyl. Representative values of $R^1$ are alkyl, cycloalkyl, cycloalkenyl, phenyl, substituted phenyl, phenylalkyl; (substituted phenyl)alkyl, phenoxyalkyl, (substituted phenoxy)alkyl, (thiophenoxy)alkyl, (thiophenoxy)alkyl, alkyl, naphthyl, bicyclo[2.2.1]heptan-2-yl, bicyclo[2.2.1]hept-5-en-2-yl and $-(CH_2)_n-Q-R^o$; wherein n is zero, 1 or 2; Q is a divalent radical derived from furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]thiophene; and $R^o$ is hydrogen or alkyl, and of $R^2$ are hydrogen, alkyl, cycloalkyl, benzyl, furyl, thienyl, pyridyl, phenyl and substituted phenyl.

Discussions of both routes are presented in U.S. Pat. No. 4,556,672, issued Dec. 3, 1985. Substituent $R^1$—CO— is attached to the oxindole nucleus by reacting the appropriate 2-oxindole or 2-oxindole-1-carboxamide with an activated derivative of acid $R^1COOH$. The activated derivative can be an acid halide, symmetrical acid anhydrides, mixed acid anhydrides mixed carboxylic-carbonic anhydrides, carboxylic acids and acyl imidazoles.

SUMMARY OF THE INVENTION

This invention provides a novel process for making 3-[hydroxy-2-(aryl)methylene]-2-oxo-1H- indole-1-carboxamides which comprises reductive debromination or deiodination (dehalogenation) of corresponding 3-(bromo- and/or iodo-substituted) 3-[hydroxy-2-(aryl)methylene]-2-oxo-1H-indole-1-carboxamides according to the equation of sequence B:

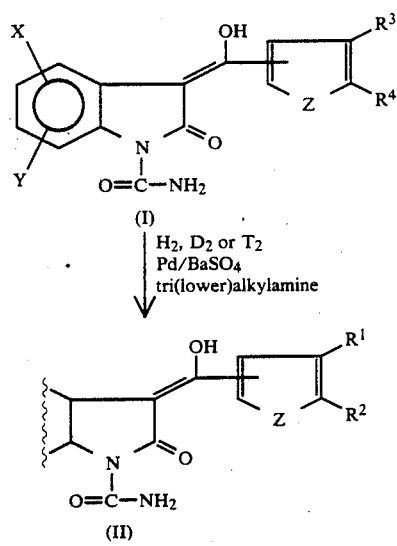

In the above equation, each of X and Y, which can be alike or different, is H, F, Cl or $CF_3$;

each of $R^3$ and $R^4$, which can be alike or different, is H, Br or I;

and Z is O or S, with the provisos that at least one of $R^3$ and $R^4$ is Br or I, when $R^1$ is deuterium, $R^2$ is deuterium or hydrogen and when $R^1$ is tritium, $R^2$ is tritium or hydrogen.

Also as part of the present invention are compounds of the formula

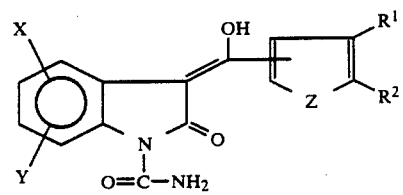

and pharmaceutically acceptable base salts where X, Y, $R^1$ and $R^2$ are as defined with the provisos that when $R^1$ is deuterium, $R^2$ is deuterium or hydrogen, when $R^1$ is tritium, $R^2$ is tritium or hydrogen and at least one of $R^1$ and $R^2$ is deuterium or tritium.

Preferred are the compounds 5-chloro-2,3-dihydro3-[hydroxy-2-[4,5-ditriteothienyl)methylene]-2-oxo -1H-indole-1-carboxamide and 5-chloro-2,3-dihydro-3-[hydroxy-2-(4,5-dideuterothienyl)methylene]-2-oxo-1H-indole-1-ca rboxamide.

The term lower alkyl applies to alkyl having one to four carbon atoms.

In sequence A, the 2-oxindoles are represented in their keto form, the form in which they are generally presented in the prior art. Sequence B, however, presents them in their tautomeric enolic form, the form in which they are now considered to predominantly exist. In this specification, it is to be understood that the particular tautomeric form used to represent the compounds of the process of this invention is immaterial; that both tautomeric forms and mixtures thereof are within the scope of this invention and the appendant claims. Further, the substituents on the exocyclic double bond at the 3-position of the compounds of formulae (I) and (II) give rise to geometric isomers. Using the Cahn-Ingold-Prelog system, the geometric isomers are referred to as the z or E forms. The present invention includes the Z and E forms of the herein described compounds and mixtures thereof.

DETAILED DESCRIPTION OF THE INVENTION

The process of this invention is readily carried out by reacting an appropriate compound of formula (I) in a reaction-inert solvent with hydrogen, deuterium or tritium in the presence of a catalyst and a tri(lower)alkylamine acid acceptor. The reaction is, for convenience and economy, conducted at room temperature. Lower or higher temperatures can be used if desired. Suitable reaction-inert solvents; i.e., solvents which do not react with reactants or products so as to adversely affect yield of desired product, are methanol, ethanol, dimethylformamide, tetrahydrofuran, dioxane, 1,2-dimethoxyethane and bis(2-methoxyethyl)ether.

The hydrogenation (or reduction) is conveniently carried out at room temperature and atmospheric pressure in a closed reaction vessel. Higher pressures can be used but are generally not resorted to in order to avoid the need for pressure equipment. Lower pressures are also avoided because of the longer reaction are also avoided because of the longer reaction times required. Similarly, higher or lower temperatures, e.g. 5° C., can be used but are generally avoided for reasons of economy.

As catalysts, palladium, platinum and rhodium can be used. The catalysts are preferably supported on, for example, carbon, barium sulfate or alumina. The preferred catalyst is palladium on barium sulfate, e.g. 5% PD/$BaSO_4$. Amounts of catalyst ranging from about 1.0 to 10.0 grams per gram of substrate are generally used.

The dehalogenated products are recovered by known procedures.

The production of hydrohalic acid (HBr or HI) as by-product of the dehalogenation reaction requires the presence of an acid acceptor. Suitable acid acceptors are organic and inorganic bases such as triethylamine, N,N-dimethylaniline, N,N-dimethylaminopyridine, 4-methylmorpholine, alkali metal acetates and carbonates. A 1-3 molar excess of acid acceptor, based on the formula (I) reactant, is generally used.

The process of the present invention provides antiinflammatory agents wherein $R^1$ and $R^2$ are each hydrogen. Those compounds made by the process of this invention wherein $R^1$ and $R^2$ are either deuterium or tritium or where both $R^1$ and $R^2$ are deuterium or tritium are useful for measuring levels of the antiinflammatory drug in various tissues. In the case of compounds containing deuterium the levels are measured by magnetic resonance. Those containing tritium are measured by radiography. Both these measuring techniques are known in the art.

The reactants of formula (I) above are prepared from appropriate reactants according to sequence A. Many of the requisite halogenated thiophene and furan carboxylic acids and activated derivatives thereof are known compounds. Those that are not known are prepared according to known methods, or methods analogous to known methods. Such methods may include the preparation of the corresponding esters or nitriles of the respective carboxylic acids in which cases hydrolysis by known procedures yields the carboxylic acid of interest. For such methods, consult: Taylor, E. C., et al., J.O.C. 50:1002 (1985); Noto, R., et al., J. Chem. Soc. P.T. II, 689 (1987); Schick, J. W., et al., J. Am. Chem. Soc. 70:286 (1948); Corral, C., et al., Heterocycles 23: 1431 (1985); Iriarte, J., et al., J. Het. Chem. 13:393 (1976); Reinecke, M. G., et al., Synthesis, 327 (1980); Lawesson, S. O., Arkiv. for Kemi. 11:317 (1957); Nemec, N., et al., Coll. Czech. Chem. Comm. 39:3527 (1974); Carpenter, A. J., et al., Tetrahedron Letters 26:1777 (1985); Satonaka, H., Bull. Chem. Soc. Japan 56:2463 (1983); Chrzaszcewska, A., Lodz. Tow. Navk. Wydz. III, 12:119 (1967) CA71:124091r (1969)). The teachings thereof are incorporated herein by reference.

EXAMPLE 1

(Z)-5Chloro-2,3-dihydro-3-[hydroxy-(2-thienyl)methylene]-2-oxo1H-indole-1-carboxamide A solution of (Z)-5-chloro-2,3-dihydro-3-[hydroxy-2-(4,5-dibromothienyl)methylene]-2-oxo-1H-indole-1-carboxamide (0.480 g, 1.0 mmoles) in methanol (45 ml) and triethylamine (0.5 ml, 3.6 mmoles) was added to a reaction vessel containing 5% Pd on barium sulfate (0.120 g) and methanol (5 ml). The reaction vessel was then connected to a hydrogenation apparatus, cycled between a vacuum and a nitrogen purge, then charged with hydrogen at one atmosphere pressure and room temperature. The reaction was stirred at a brisk rate and hdyrogen supplied at one atmosphere over an eight hour period. Thin layer chromatography (tetrahydrofuran) of the reaction showed only a single spot and no starting material. The reaction was stopped and the homogeneous green solution filtered through a diatomaceous earth pad. The pad was washed with methanol until the filtrate was diluted with water (100 ml), evaporated to remove the methanol and the remaining aqueous solution basified with solid sodium bicarbonate (4.200 g, 50.0 mmoles). The basic solution was then acidified to pH <3 with concentrated hydrochloric acid. The product precipitated and was recovered by filtration, washed with water and dried to afford the title product (0.290 g, 0.9 mmoles; 90% yield) as a yellow solid; m.p. 224° C. (dec.).

EXAMPLE 2

(Z)-5-Fluoro-6-chloro-2,3-dihydro-3-[hydroxy-(2-thienyl)methylene]-2-oxo-1H-indole-1-carboxamide Following the procedure of Example 1, (Z)-5-fluoro-6-chloro-2,3-dihydro-3-[hydroxy-2-(4,5-dibromothienyl)methylene]-2-oxo-1H-indole-1-carboxamide (0.496 g, 1.0 mmoles) was converted to the title product (0.305 g, 0.9 mmoles, 90% yield); m.p. 239°-241° C.

EXAMPLE 3

The compounds listed below are dehalogenated mutatis mutandi according to the procedure of Example 1.

| X | Y | Z | $R^3$ | $R^4$ |
|---|---|---|---|---|
| 5-Cl | H | S | Br | H |
| 5-Cl | H | S | H | Br |
| 5-F | 6-Cl | S | Br | H |
| 5-F | 6-Cl | S | H | Br |
| 5-F | 6-Cl | S | H | I |
| 5-Cl | H | S | I | H |
| 5-F | 6-Cl | O | H | Br |

EXAMPLE 4

5-Chloro-2,3-dihydro-3-[hydroxy-2-(4,5-dideutero-thienyl)methylene]-2-oxo-1H-indole-1-carboxamide A solution of 0.48 g (1.0 mmoles) of 5-chloro-2,3-dihydro-3-[hydroxy-2-(4,5-dibromothienyl)methylene]-2oxo-1H-indole-1carboxamide in 45 ml of methanol-$d_4$ (99.5 atom % deuterium) containing 0.5 ml (3.6 mmoles) of triethylamine was charged to a flask containing 0.12 g of 5% palladium on barium sulfate. The flask was connected to an atmospheric hydrogenation apparatus, and the contents of the flask hydrogenated atmospherically with deuterium gas for 16 hours at room temperature. The catalyst was then filtered off through a pad of diatomaceous earth, the filtrate diluted with 100 ml of distilled water and the methanol removed in vacuo. The aqueous residue was stirred while 4.2 g (50.0 mmoles) of powdered, anhydrous sodium bicarbonate was added. After stirring for a few minutes, the basic solution was acidified (concentrated hydrochloric acid), causing precipitation of an orange solid. The solid was filtered off, washed with water and dried to afford desired product as an orange solid weighing 309 mg (0.96 mmoles, 96% yield); m.p. 220°–223° C. (dec.), which was shown to be 91% isotopically pure by NMR.

The produce had the following physicochemical characteristics: El Ms (m/z): 322/324 (M+, 4%), 279/281 (M+-CONH, 11%), 193/195 (M+-CONH-C4H2D2S, base), 170 (58%) and 113 (60%). $^1$H-NMR (DMSO-$d_6$) delta, 8.1 (d, 1H, J=8.7 Hz), 8.06 (s, 1H), 7.9 (s, 1H), 7.1 (d, 1H, J=8.7 Hz), and 4.9 (broad exchangeable).

EXAMPLE 5

5-Chloro-2,3-dihydro-3-[hydroxy-2-(4,5-ditriteo-thienyl)methylene]-2-oxo-1H-indole-1-carboxamide A solution of 5.7 mg (0.012 mmoles) of 5-chloro-2,3-dihydro-3-[hydroxy-2-(4,5-dibromothienyl)methylene]-2-oxo-1H-indole-1-carboxamide in 1 ml of methanol containing 6 µl of triethylamine was charged to a flask containing 1.4 mg of 5% palladium on barium sulfate. The reaction was hydrogenated atmospherically with tritium gas for 4 hours at room temperature. The catalyst was then filtered off through diatomaceous earth, the filtrate diluted with distilled water and the methanol removed in vacuo. HPLC purification [Zorbax RX column, 1% Et3NHOAc pH 4/CH3CN (65:35)] provided pure tritiated material in solution. Evaporation to an aqueous solution and dilution with an equivalent volume of ethanol to 25 ml provided a radioactive concentration of 8.5 mCi/ml at 47.9 Ci/mmol specific activity. The level of tritium incorporation was calculated to be greater than 75%. The produce was identical to non-radioactive standard by HPLC and TLC.

Physicochemical characteristics: $^3$H-NMR (MeOH, 320 MHz) delta, 7.59 (1H, d, J=5.2 Hz) and 7.13 (1H, d, J=5.2 Hz).

PREPARATION A

5-Chloro-2,3-dihydro-3-[hydroxy-2-(3-bromothienyl)-methylene]-2-oxo-1H-indole-1-carboxamide 2.07 g (10.0 mmoles) of 3-bromo-2-thiophenecarboxylic acid was reacted at reflux with 1.1 ml (15.0 mmoles) of thionyl chloride. After 1.5 hours refluxing, excess thionyl chloride was evaporated, leaving 2.27 g of crude acid chloride as a solid. A 10 ml N,N-dimethylformamide solution of 2.27 g (10.0 mmoles) of 3-bromo-2-thiophenecarbonyl chloride was reacted with 1.75 g (8.33 mmoles) of 5-chloro-2,3-dihydro-2-oxo-1H-indole-1-carboxamide in the presence of 3.05 g (25.0 mmoles) of 4-(N,N-dimethylamino)pyridine in 40 ml of N,N-dimethylformamide. Reaction workup gave 3.28 g of a dark orange solid. Recrystallization of this solid gave 1.63 g (4.08 mmoles, 41% yield) of the title compound as an orange crystalline solid, m.p. 216°–217° C. (2-butanone).

Analysis: Calculated for $C_{14}H_8BrClN_2O_3S$: C, 42.08; H, 2.02; N, 7.01%. Found: C, 42.15; H, 2.05; N, 7.00%. ACE-EIMS (m/z): 398/400/402 M+, 8%), 355/357/359 (M+-CHNO, 21%), 276/278 (M+-CHNO-Br, 13%), 193/195 ($M^{30}$ -CHNO-C4H3BrS, 89%) and 69 (unknown, base). $^1$HNMR (DMSO-$d_6$) keto form: delta, 8.25 (1H, br s, exchangeable), 8.10 (1H, d, J=8.5Hz), 7.87 (1H , d, J=5Hz), 7.81 (1H, br d, J=1.5Hz), 7.54 (1H, br s, exchangeable), 7.21 (2H, m) and 5.70 (1H, br s, exchangeable); enol form: delta, 10.27 (1H, br s, exchangeable), 8.19 (1H, br s, exchangeable), 8.13 (1H, d, J=8.5Hz), 7.91 (1H, d, J=5Hz), 7.81 (1H, br d, J=1.5Hz), 7.60 (1H, br s, exchangeable), 7.25 (1H, dd, J=8.5, 1.5Hz) and 7.23 (1H, d, J=5Hz); $^{13}$CNMR (DMSO-$d_6$) delta, 167.0, 162.2, 152.4, 134.6, 131.4, 130.2, 129.8, 127.6, 125.5, 124.9, 121.1, 116.0, 111.5 and 103.8; ir (potassium bromide): 3375, 3217 br, 1726, 1617, 1583, 1752, 1374, 1267 and 1196 cm$^{-1}$.

PREPARATION B

5-Chloro-2,3-dihydro-3-[hydroxy-2-(4-bromothienyl)-methylene]-2-oxo-1H-indole-1-carboxamide According to the procedure of Preparation A, 2.48 g (12.0 mmoles) of 4-bromo-2-thiophenecarboxylic acid (prepared according to Lawesson, S. O., Arkiv. for Kemi. 11:317 (1957)) and 10 ml of thionyl chloride were combined and heated. The reaction gave 2.99 g of 4-bromo-2-thiophenecarbonyl chloride as a dark oil. The acid chloride, 2.11 g (10.0 mmoles) of 5-chloro-2,3-dihydro-2-oxo-1H-indole-1-carboxamide and 3.67 g (30.0 mmoles) of 4-(N,N-dimethylamino)pyridine were reacted in N,N-dimethylformamide to give 4.03 g of a crude orange solid. Recrystallization gave 2.67 g (6.68 mmoles, 66.8% yield) of title compound as a yellow crystalline solid, m.p. 217°–219° C. (dec.) (2-butanone).

Analysis: Calculated for $C_{14}H_8BrClN_2O_3S$: C, 42.08; H, 2.02; N, 7.01%. Found: C, 42.07; H, 2.00; N, 7.04%. EIMS (m/z): 398/400/402 (M+, 1%), 355/357/359 (M+-CHNO, 8%), 193/195 ($M^{30}$ -CHNO-$C_4H_3BrS$, base) and 189/191 ($C_5H_2BrOS$, 35%); $^1$HNMR (DMSO-$d_6$) delta, 8.41 (1H, d, J=1.6Hz), 8.06 (1H, br d, J=1.2Hz), 8.05 (1H, d, J=8.5Hz), 7.86 (1H, br s), 6.98 (1H, dd, J=8.5, 1.2Hz) and 6.05 (br s, exchangeable); ir (potassium bromide): 3384, 3228 br, 1741, 1620, 1588, 1573, 1375, 1269, 1193 and 1180 cm$^{-1}$.

PREPARATION C

5-Chloro-2,3-dihydro-3-[hydroxy-2-(5-bromothienyl)-methylene]-2-oxo-1H-indole-1-carboxamide Following the procedure of Preparation A, 2.07 g (10.0 mmoles) of commercially available 5-bromo-2-thiophenecarboxylic acid was reacted with 10 ml of thionyl chloride to give 2.35 g of crude 5-bromo-2-thiophenecarbonyl chloride as a red oil. The total crude acid chloride was coupled to 1.76 g (8.33 mmoles) of 5-chloro-2,3-dihydro-2-oxo-1H-indole-1-carboxamide by the procedure in Preparation A using 3.05 g (25.0 mmoles) of 4-(N,N-dimethylamino)pyridine and 50 ml of N,N-dimethylformamide. Acidic workup gave a solid which was recrystallized to give 1.77 g (4.43 moles, 53% yield) of title compound as reddish-brown crystals, m.p. 228°–229° C. (tetrahydrofuran).

Analysis: Calculated for $C_{14}H_8BrClN_2O_3S$: C, 42.08; H, 2.02; N, 7.01%. Found: C, 42.25; H, 1.97; N, 6.77%. ACE-EIMS (m/z): 397/399/401 ($M^{30}$, 5%), 354/356/358 M+-CHNO, 17%) and 193/195 (M+-CONH-$C_4H_3BrS$, base); $^1$HNMR (DMSO-$d_6$) delta, 8.19 (1H, d, J=4Hz), 8.08 (1H, d, J=8.06 (1H, br s), 7.29 (1H, br d, J=4Hz), 7.02 (1H, br d, J=8.5Hz) and 6.24 (1H, br s, exchangeable); ir (potassium bromide): 3386, 3208 br, 1750, 1569, 1375, 1344, 1203 and 794 cm$^{-1}$.

PREPARATION D

5-Chloro-2,3-dihydro-3-[hydroxy-2-(5-iodothienyl)methylene]-2-oxo-1H-indole-1-carboxamide Following the procedure of Preparation A, 1.96 g (7.72 mmoles) of 5-iodo-2-thiophenecarboxylic acid (J. W. Schick, J. Am. Chem. Soc. 70, 286 (1948)) was mixed with 10 ml of thionyl chloride and heated to reflux. Reaction led to 2.10 g of crude 5-iodo-2-thiophenecarbonyl chloride as a yellow solid. This yellow solid was dissolved in 10 ml of N,N-dimethylformamide and slowly added to a 40 ml N,N-dimethylformamide solution of 1.75 g (8.33 mmoles) of 5-chloro-2,3-dihydro-2-oxo-1H-indole-1-carboxamide and 3.05 g (25 mmoles) of 4-(N,N-dimethylamino)pyridine. Workup gave 3.18 g of impure product as an orange solid. Recrystallization in tetrahydrofuran gave 1.47 g (3.29 mmoles, 40% yield) of pure title compound as fine orange crystals, m.p. 230°–332° C.

Analysis: Calculated for $C_{14}H_8ClIN_2O_3S$: C, 37.65; H, 1.81; N, 6.27%. Found: C, 37.93; H, 1.73; N, 6.13%. EIMS (m/z): 446/448 (M+-CHNO, 13%), 237 $C_5H_2IOS$, 39%) and 193/195 (M+-CONH-$C_4H_3IS$, base); $^1$HNMR (DMSO-$d_6$) delta, 8.05 (1H, d, J=8.5Hz), 8.00 (1H, br s), 7.92 (1H, d, J=4.0Hz), 7.38 (1H, br d, J=4.0Hz), 7.01 (1H, br d, J=8.5Hz) and 5.37 (1H, br s, exchangeable); ir (potassium bromide): 3383 br, 3216 br, 1749, 1565 and 1373 cm$^{-1}$.

PREPARATION E

5-Chloro-2,3-dihydro-3-[hydroxy-2-(4,5-dibromothienyl)methylene]-2-oxo-1H-indole-1-carboxamide Using the procedure of Preparation A, 2.86 g (10.0 mmoles) of commercially available 4,5-dibromo-2-thiophenecarboxylic acid was added to 10 ml of thionyl chloride to give a heterogeneous mixture. Heating the reaction mixture helped the solution become homogenous. Concentration of the reaction solution gave 3.15 g of crude 4,5-dibromo-2-thiophenecarbonyl chloride as a brown oil. The crude acid chloride, dissolved in 10 ml of N,N-dimethylformamide was slowly added to 1.76 g (8.33 mmoles) of 5-chloro-2,3-dihydro-2-oxo-1H-indole-1-carboxamide and 3.05 g (25.0 mmoles) of 4-(N,N-diemthylamino)pyridine in 40 ml of N,N-dimethylformamide. Workup gave 2.82 g of orange solid which was recrystallized from 2-butanone to give 1.61 g (3.37 mmoles, 40% yield) of pure title compound as yellow solid, m.p. 229°–231° C.

Analysis: Calculated for $C_{14}H_7Br_2ClN_2O_3S$: C, 35.14; H, 1.47; N, 5.85%. Found: C, 35.34; H, 1.34; N, 5.66%. ACE/EIMS (m/z): 476/478/480/482 (M+, 4%), 433/435/437/439 ($M^{30}$ -CHNO, 23%), 267/269/271 ($C_5HBr_2OS$, 28%) and 193/195 (M+-CONH-$C_4H_2Br_2S$, base); $^1$HNMR (DMSO-$d_6$) delta, 8.62 (1H, s), 8.14 (1H, br s), 8.05 (1H, d, J=8.5Hz), 6.93 (1H, br d, J=8.5Hz) and 6.86 (1H, br s, exchangeable); ir (potassium bromide): 3397, 3238 br, 1748, 1614, 1574, 1375, 1193 and 816 cm$^{-1}$.

PREPARATION F

6-Chloro-5-fluoro-3-[hydroxy-2-(4,5-dibromothienyl)-methylene]-2-oxo-1H-indole-1-carboxamide To a solution of 4-(dimethylamino)pyridine (1.61 g, 13.2 mmoles) in N,N-dimethylformamide (15 ml) was added 6-chloro-5-fluoro-2,3-dihydro-2-oxo-1H-indole-1-carboxamide (1.0 g, 4.4 mmoles). The mixture was stirred and cooled in an ice-water bath to 5° C. and placed under a nitrogen atmosphere. A solution of 4,5-dibromo-2-thiophene carboxylic acid chloride in N,N-dimethylformamide (5 ml) was added dropwise to the stirred mixture. Upon completion of the addition, stirring was continued for 105 minutes after which the mixture was poured into 1N HCl (150 ml) with stirring. The precipitate which formed was filtered off, washed with water and air-dried. Yield=2.37 g of brownish-yellow solid; m.p. 193°–196° C. The solid was taken up in boiling acetic acid (75 ml) and the solution filtered hot. Upon cooling to room temperature, the recrystallized solid was filtered off, washed with acetic acid and then with hexane. It was dried overnight with heating isopropanol under high vacuum. Yield = 1.35 g of fluffy yellow solid; m.p. 226–228° C. (dec).

Analysis calculated for $C_{14}H_6Br_2ClFN_2O_3S$: C, 33.87; H, 1.22; N, 5.46. Found: C, 33.99, H, 1.14; N, 5.53.

PREPARATION G

5-Chloro-2,3-dihydro-3-[hydroxy-2-(5-bromofuryl)methylene]-2-oxo-1H-indole-1-carboxamide Using the procedure of Preparation A, 1.91 g (10.0 mmoles) of commercially available 5-bromo-2-furancarboxylic acid was dissolved in 10 ml of thionyl chloride and heated to reflux under nitrogen for 1 hour and the acid chloride product was recovered. A 40 ml N,N- dimethylformamide solution of 1.75 g (8.3 mmoles) of 5-chloro-2,3-dihydro-2-oxo-1H-indole-1-carboxamide and 3.05 g (25 mmoles) of 4-(N,N-dimethylamino)pyridine was reacted with 2.09 g (10 mmoles) of 5-bromo-2furan carbonyl chloride in 10 ml of N,N-dimethylformamide. After a reaction time of about 45 minutes, the mixture was acidified by pouring into 250 ml of 1N HCl. The produce was recrystallized from acetic acid, washed with acetic acid, then hexane and dried overnight in vacuo at room temperature. The resulting product was then dried with low heat under high vacuum to yield 1.37 g of the title compound.

Analysis: Calculated for $C_{14}H_8BrClN_2O_4$: C, 43.84; H, 2.10; N, 7.30. Found: C, 43.94, H, 2.02, N, 7.16%; EIMS (m/z): 382/384 (N+, 10%), 339/341 $M^{+-CONH}$, 35%) and 193/195 ($M^+$ -CONH-$C_4H_3BrO$, base); $^1$HNMR (DMSO-$d_6$) delta 8.50 (exchangeable), 8.08 (1H, d, J=8.5Hz), 8.00 (1H, br s), 7.81 (1H, d, J=3.5Hz), 7.63 (1H, exchangeable), 7.16 (1H, br d, J=8.5Hz), 6.90 (1H, d, J=3.5Hz) and 5.04 (exchangeable); IR (potassium bromide) 3382, 3220, 1735, 1723, 1620, 1587, 1533, 1464, 1379 and 1022 cm$^{-1}$.

We claim:

1. Process for making compounds of the formula

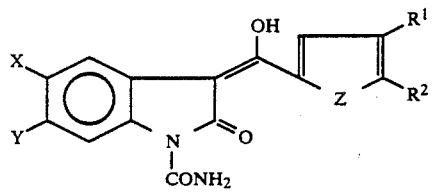

wherein X and Y are each hydrogen, chloro or fluoro; $R^1$ and $R^2$ are each hydrogen, deuterium or tritiium; and Z is O or S which comprises the reductive dehalogenation of a compound of the formula

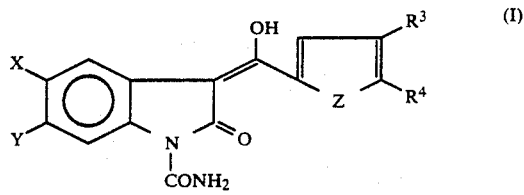

wherein $R^3$ and $R^4$ are each hydrogen, bromo or iodo using hydrogen, deuterium or tritium gas and a Pd/BaSO$_4$ catalyst in a reaction-inert solvent containing a 1-3 molar excess, based on the reactant of formula I, of a tri(lower)alkylamine with the provisos that (1) at least one of $R^3$ and $R^4$ is bromo or iodo; and wherein (2) when $R^1$ is deuterium, $R^2$ is deuterium or hydrogen; and wherein (3) when $R^1$ is tritium, $R^2$ is tritium or hydrogen.

2. A process according to claim 1 wherein the reductive dehalogenation is conducted at atmospheric pressure and room temperature and the tri(lower)alkylamine is triethylamine.

3. The process according to claim 2 wherein X is chloro and Y is hydrogen and each of $R^3$ and $R^4$ is bromo.

4. The process according to claim 2 wherein X is fluoro, Y is chloro, and each of $R^3$ and $R^4$ is bromo.

5. A compound of the formula

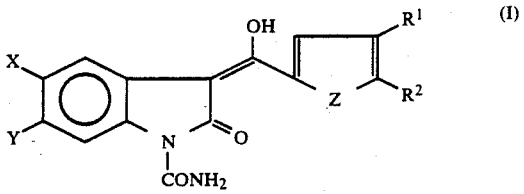

and a pharmaceutically acceptable salt thereof wherein X and Y are each hydrogen, chloro or fluoro; Z is O or S; and $R^1$ and $R^2$ are each hydrogen, deuterium or tritium with the provisos that (1) when $R^1$ is deuterium, $R^2$ is deuterium or hydrogen; and wherein (2) when $R^1$ is tritium $R^2$ is tritium or hydrogen; and wherein (3) at least one of $R^1$ and $R^2$ is deuterium or tritium.

6. A compound of claim 5, 5-chloro-2,3-dihydro-3-[hydroxy-2-(4,5-ditriteothienyl)methylene]-2-oxo-1H-indole-1-carboxamide.

7. A compound of claim 5, 5-chloro-2,3-dihydro-3-[hydroxy-2-(4,5-dideuterothienyl)methylene]-2-oxo-1H-indole-1-carboxamide.

* * * * *